(12) United States Patent
Fushimi

(10) Patent No.: US 7,915,441 B2
(45) Date of Patent: Mar. 29, 2011

(54) OLIGOPHOSPHAZENE COMPOUND

(75) Inventor: Toshiki Fushimi, Marugame (JP)

(73) Assignee: Fushimi Pharmaceutical Co., Ltd., Kagawa (JP)

( * ) Notice: Subject to any disclaimer, the term of this patent is extended or adjusted under 35 U.S.C. 154(b) by 3 days.

(21) Appl. No.: 12/338,710

(22) Filed: Dec. 18, 2008

(65) Prior Publication Data

US 2010/0160599 A1    Jun. 24, 2010

(51) Int. Cl.
*C07F 9/02* (2006.01)

(52) U.S. Cl. ............ 558/75; 528/399; 528/75; 528/486; 526/262; 526/275; 526/276; 548/956

(58) Field of Classification Search .................. 528/399, 528/75, 398, 486; 526/262, 275, 276; 548/956; 558/75

See application file for complete search history.

(56) References Cited

U.S. PATENT DOCUMENTS 5,705,668 A * 1/1998 Odello et al. .................. 558/80

FOREIGN PATENT DOCUMENTS

JP    7-198967 A    8/1995

OTHER PUBLICATIONS

Olshavsky et al., Macromolecules 1997, vol. 30, No. 14, pp. 4179-4183.
Allcock et al., Inorganic Chemistry Jun. 1966, vol. 5, No. 6, pp. 1016-1020.

* cited by examiner

*Primary Examiner* — Randy Gulakowski
*Assistant Examiner* — Shane Fang
(74) *Attorney, Agent, or Firm* — Birch, Stewart, Kolasch & Birch, LLP

(57) ABSTRACT

The oligophosphazene compound capable of forming a polymer which can be used as an optical material is a cyclic or linear compound including constituent units represented by the general formula (I) below in a range from 3 to 14. In the general formula (I), k is an integer of 1 to 4 and $X^1$ is one selected from the group consisting of an oxygen atom, a sulfur atom, an NH group and an $NCH_3$ group. A polymer made of this oligophosphazene compound exhibits high transparency and a high refractive index and is also less likely to cause optical dispersion, and thus it can be used as an optical lens, a retardation film, a light transmission body and other optical moldings.

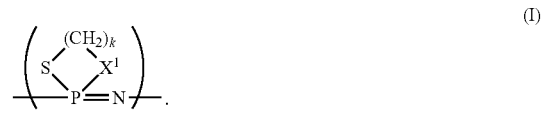

(I)

15 Claims, No Drawings

OLIGOPHOSPHAZENE COMPOUND

FIELD OF THE INVENTION

The present invention relates to an oligophosphazene compound, and particularly to an oligophosphazene compound capable of forming a polymer which can be used as an optical material.

BACKGROUND ART

Since phosphazene compounds, especially cyclic and linear oligophosphazene compounds contain phosphorus atoms, they are expected to show a high refractive index when used as an optical material. Thus some documents suggest application to optical materials having high refractive indices. For example, Macromolecules 1997, 30, 4179-4183 describes that a linear polyphosphazene compound including more than 1,000 phosphazene units (—N=P—) in which phenyl groups, naphthoxy groups, halogenated phenyl groups, halogenated naphthyl groups, derivatives thereof or the like are bonded to the phosphorus atoms of the phosphazene skeleton can be used as an optical material. This polyphosphazene compound exhibits a high refractive index of more than 1.6, but exhibits an Abbe number of about 25 at most because of the aromatic rings in the structure, thus causing large optical dispersion. Abbe number is an index of optical dispersion. The larger the numerical value, the smaller the optical dispersion becomes.

Further, a Japanese Unexamined Patent Publication No. 7-198967 describes a light transmission body in which a transparent clad material is filled with a liquid of an oligophosphazene compound. The oligophosphazene compound used herein is a compound in which alkoxyl groups, aryloxy groups, amino groups, derivatives thereof or the like are bonded to the phosphorus atoms of the phosphazene skeleton, and exhibits high transparency through a wide wavelength range including the ultraviolet region, the visible region and the infrared region. Since this oligophosphazene compound is a liquid, it can be used as an optical material to be filled in the above clad material, but is impractical to be used as a material for optical molding such as an optical lens.

An object of the present invention is to realize an oligophosphazene compound capable of forming a transparent polymer which has a high refractive index and a high Abbe number, and thus is usable as an optical material.

SUMMARY OF THE INVENTION

An oligophosphazene compound of the present invention includes at least one sulfur-containing ring containing a phosphorus atom of a phosphazene skeleton as a constituent atom, wherein the sulfur-containing ring is composed of a residue of a difunctional alkylthiol compound having a thiol group and a group selected from the group consisting of an amino group, a hydroxyl group and a mercapto group.

One aspect of the oligophosphazene compound of the present invention includes a constituent unit U1 represented by the following general formula (I). The constituent units U1 included in the oligophosphazene compound of this aspect may be the same or different.

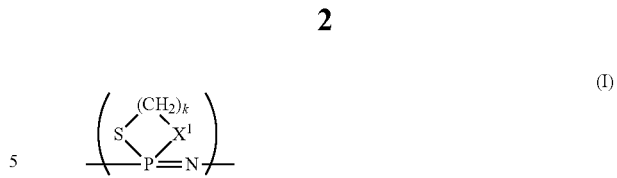

In the general formula (I), k is an integer of 1 to 4. Further, $X^1$ is one selected from the group consisting of an oxygen atom, a sulfur atom, an NH group and an $NCH_3$ group.

In the oligophosphazene compound of this aspect, the number m of the constituent unit U1 included is usually an integer of 3 to 14. Further, the oligophosphazene compound of this aspect is preferably a cyclic oligophosphazene compound in which the constituent units U1 are circularly linked.

The oligophosphazene compound of this aspect may further include a constituent unit U2 represented by the following general formula (II). The constituent unit U2 included in the oligophosphazene compound of this aspect may be the same or different.

In the general formula (II), each of $X^2$ and $X^3$ is one selected from the group consisting of an oxygen atom, a sulfur atom, an NH group and an $NCH_3$ group. $R^1$ and $R^2$ each represents a group represented by the following general formula (III).

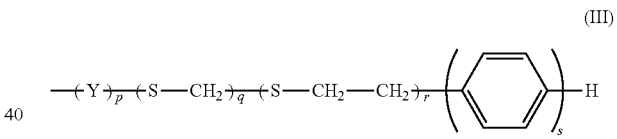

In the general formula (III), Y represents one group among the group of a methylene group and an ethylene group. Further, p is 0 or 1, each of q and r is an integer of 0 to 5, and s is 0 or 1. In the general formula (III), the order of each constituent unit, that is, a methylene group or an ethylene group represented by Y, a thiomethylene group, a thioethylene group and a phenylene group is optional.

The oligophosphazene compound of this aspect is preferably an oligophosphazene compound in which both the number m of the constituent unit U1 included and the number n of the constituent unit U2 included are integers and satisfy a relation: $3 \leq m+n \leq 14$, and particularly preferably a cyclic oligophosphazene compound in which the constituent unit U1 and the constituent unit U2 are circularly linked. Regarding this cyclic oligophosphazene compound, in the general formula (I), k is 2 or 3, the number m of the constituent unit U1 included and the number n of the constituent unit U2 included satisfy a relation $3 \leq m+n \leq 4$, all of $X^1$, $X^2$ and $X^3$ are NH groups and, in the general formula (III), p is 1, q is 0 or 1 and both r and s are 0.

The oligophosphazene compound of the present invention polymerizes by ring-opening of the sulfur-containing ring through heating, resulting in a moldable polymer. This polymer has a high refractive index and a high Abbe number since the oligophosphazene compound serving as the material of the polymer has phosphorus atoms and sulfur atoms having high electron densities and also has high transparency through a wide wavelength range including ultraviolet region, visible region and infrared region. Therefore, the polymer of the oligophosphazene compound of the present invention is useful as various optical materials, especially as materials for optical moldings.

More specifically, the polymer obtained by thermally polymerizing the oligophosphazene compound of the present invention can be used as a material for optical lenses, retardation films and light transmission bodies.

A method for producing an oligophosphazene compound according to the present invention includes the step A of applying at least one of the following steps (a-1) and (a-2) to a phosphazene compound including a phosphonitrile dihalide unit represented by the following general formula (IV):

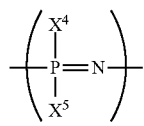

in the general formula (IV), $X^4$ and $X^5$ each represents a halogen atom.

step (a-1): the step of nucleophilically substituting halogen atoms of the phosphonitrile dihalide unit using at least one kind of compound among the group of difunctional alkylthiol compounds having a thiol group and a group selected from the group consisting of an amino group, a hydroxyl group and a mercapto group in the presence of a base capable of scavenging a hydrogen halide.

step (a-2): the step of nucleophilically substituting halogen atoms of the phosphonitrile dihalide unit using a metal salt of at least one kind of compound among the group of difunctional alkylthiol compounds having a thiol group and one group among the group of a hydroxyl group and a mercapto group.

According to this method, an oligophosphazene compound including the constituent unit U1 of the present invention can be produced.

This method may further include the step B of applying at least one step of the following step (b-1) and step (b-2) to the above-mentioned phosphazene compound including the phosphonitrile dehalide unit.

step (b-1): the step of nucleophilically substituting halogen atoms of the phosphonitrile dihalide unit using at least one kind of compound selected from the group consisting of a monofunctional alkyl compound having a group selected from the group consisting of an amino group, a hydroxyl group and a mercapto group, a monofunctional thioalkyl compound having a group selected from the group consisting of an amino group, a hydroxyl group and a mercapto group, a monofunctional phenyl compound having a group selected from the group consisting of an amino group, a hydroxyl group and a mercapto group and ammonia in the presence of a base capable of scavenging a hydrogen halide.

step (b-2): the step of nucleophilically substituting halogen atoms of the phosphonitrile dihalide unit using at least one kind of compound selected from the group consisting of a metal salt of a monofunctional alkyl compound having one group among the group of a hydroxyl group and a mercapto group, a metal salt of a monofunctional thioalkyl compound having one group among the group of a hydroxyl group and a mercapto group and a metal salt of a monofunctional phenyl compound having one group among the group of a hydroxyl group and a mercapto group.

According to the method of this aspect, an oligophosphazene compound including both the constituent unit U1 and the constituent unit U2 of the present invention can be produced.

The oligophosphazene compound including the phosphonitrile dihalide unit used in the production method is preferably a cyclic oligophosphazene compound in which the phosphonitrile dihalide units are circularly linked.

Other objects and effects of the present invention will be described in the following detailed description.

DETAILED DESCRIPTION OF THE INVENTION

The oligophosphazene compound of the present invention includes at least one sulfur-containing ring containing a phosphorus atom of a phosphazene skeleton as a constituent atom, wherein the sulfur-containing ring composed of a residue of a difunctional alkylthiol compound having a thiol group and a group selected from the group consisting of an amino group, a hydroxyl group and a mercapto group. One aspect of the oligophosphazene compound includes more than one constituent unit U1 represented by the following formula (I) (hereinafter oligophosphazene compound of this aspect may be referred to as "oligophosphazene compound of the aspect 1").

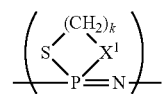

In the general formula (I), k is an integer of 1 to 4, preferably 2 or 3, and particularly preferably 2. $X^1$ is one selected from the group consisting of an oxygen atom, a sulfur atom, an NH group and an $NCH_3$ group. $X^1$ is preferably an NH group or an $NCH_3$ group, and is particularly preferably an NH group.

The oligophosphazene compound of the aspect 1 may be either a cyclic oligophosphazene compound in which the constituent units U1 are circularly linked, a mixture of more than one kind of cyclic oligophosphazene compound, a linear oligophosphazene compound in which the constituent units U1 are linearly linked, a mixture of more than one kind of linear oligophosphazene compound, or a mixture of one or more than one kind of cyclic oligophosphazene compound and one or more than one kind of linear oligophosphazene compound. The oligophosphazene compound of the aspect 1 is preferably composed of only one kind of cyclic oligophosphazene compound, or a mixture of more than one kind of cyclic oligophosphazene compound.

In the oligophosphazene compound of the aspect 1, the cyclic oligophosphazene compound is substantially composed only of the constituent unit U1, while the constituent unit U1 located at the end has a certain terminal structure in the case of the linear oligophosphazene compound, for example, as described below.

The terminal structure at the phosphorus atom side:

The terminal structure at the nitrogen atom side:

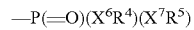

or

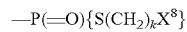

In these terminal structures, each of $X^6$, $X^7$ and $X^8$ is one selected from the group consisting of an oxygen atom, a sulfur atom, an NH group and an NCH$_3$ group. Among these, an NH group and an NCH$_3$ group are preferred and an NH group is particularly preferred. $X^6$, $X^7$ and $X^8$ may be the same or different. $R^3$, $R^4$ and $R^5$ are the same groups as those represented by the general formula (III) described below. P{S(CH$_2$)$_k$X$^8$} forms the same ring structure as that included in the general formula (I).

In the oligophosphazene compound of the aspect 1, the number of the constituent unit U1 is preferably from 3 to 14, more preferably from 3 to 6, and particularly preferably from 3 to 4. Further, the oligophosphazene compound of the aspect 1 may include a single kind of constituent unit U1 having the same sulfur-containing ring containing the phosphorus atom of the phosphazene skeleton as its constituent atom, or more than one kind of constituent unit U1 each having a different sulfur-containing ring, in the entire constituent units U1.

The oligophosphazene compound according to another aspect of the present invention further includes, in addition to the above constituent unit U1, a constituent unit U2 represented by the following general formula (II) (hereinafter the oligophosphazene compound of this aspect may be referred to as "oligophosphazene compound of the aspect 2"). The oligophosphazene compound may include one constituent unit U2, or more than one constituent unit U2. In the latter case, the constituent unit U1 and the constituent unit U2 may be alternately arranged, or may be arranged at random. When they are alternately arranged, both constituent units may form a block in which more than one of either the constituent unit U1 or U2 are linked.

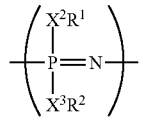
(II)

In the general formula (II), each of $X^2$ and $X^3$ is one selected from the group consisting of an oxygen atom, a sulfur atom, an NH group and an NCH$_3$ group. Among these, an NH group and an NCH$_3$ group are preferred and an NH group is particularly preferred. $X^2$ and $X^3$ may be the same or different.

In the general formula (II), each of $R^1$ and $R^2$ is a group represented by the following general formula (III).

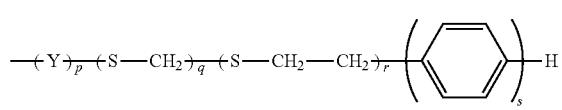
(III)

In the general formula (III), Y represents a methylene group or an ethylene group. p is 0 or 1. Each of q and r is an integer of 0 to 5 and preferably satisfies a relation of $0 \leq q+r \leq 2$. s is 0 or 1. Further, in the general formula (III), the order of each constituent unit is optional. More specifically, in the general formula (III), the order of each constituent unit, that is, a methylene or an ethylene group represented by Y, a thiomethylene group, a thioethylene group and a phenylene group may appropriately be changed as long as a hydrogen atom is located at the end.

In the constituent unit U2, $R^1$ and $R^2$ may be the same or different.

Specific examples of the group represented by the general formula (III) include a hydrogen atom, a methyl group, an ethyl group, a (methylthio)methyl group, a 2-(methylthio)ethyl group, an (ethylthio)methyl group, a 2-(ethylthio)ethyl group, a (methylthio)methylthio group, a [(methylthio)methylthio]methyl group, a 2-[(methylthio)methylthio]ethyl group, a [2-(methylthio)ethylthio]methyl group, a 2-[2-(methylthio)ethylthio]ethyl group, an (ethylthio)methylthio group, an [(ethylthio)methylthio]methyl group, a 2-[(ethylthio)methylthio]ethyl group, a [2-(methylthio)ethylthio]methyl group, a [2-(ethylthio)ethylthio]methyl group, a 2-[2-(ethylthio)ethylthio]ethyl group and a phenyl group. Among these specific examples, a hydrogen atom, a methyl group, an ethyl group, a 2-(methylthio)ethyl group, a 2-[(methylthio)methylthio]ethyl group, a 2-[2-(methylthio)ethylthio]ethyl group and a phenyl group are preferred, and a hydrogen atom, a methyl group, an ethyl group and a 2-(methylthio)ethyl group are particularly preferred.

In the oligophosphazene compound of the aspect 2, both the number m of the constituent unit U1 included and the number n of the constituent unit U2 included are integers. Further, the numbers m and n preferably satisfy a relation of $3 \leq m+n \leq 14$, particularly preferably satisfy relations of $m \geq 2$ and $3 \leq m+n \leq 6$, and more preferably satisfy relations of $m \geq 2$ and $3 \leq m+n \leq 4$.

The oligophosphazene compound of the aspect 2 may be either a cyclic oligophosphazene compound in which the constituent unit U1 and the constituent unit U2 are circularly linked, a mixture of more than one kind of cyclic oligophosphazene compound, a linear oligophosphazene compound in which the constituent unit U1 and the constituent unit U2 are linearly linked, a mixture of more than one kind of linear oligophosphazene compound, or a mixture of one or more than one kind of cyclic oligophosphazene compound and one or more than one kind of linear oligophosphazene compound. The oligophosphazene compound of this aspect is preferably composed of only one kind of cyclic oligophosphazene compound, or a mixture of more than one kind of cyclic oligophosphazene compound.

In the oligophosphazene compound of the aspect 2, the cyclic oligophosphazene compound is substantially composed only of the constituent unit U1 and the constituent unit U2, while the constituent unit U1 and the constituent unit U2 located at the end have a certain terminal structure at the phosphorus atom side and the nitrogen atom side in the case of the linear oligophosphazene compound. Examples of the terminal structure at the phosphorus atom side and the terminal structure at the nitrogen atom side are the same as those in case of the oligophosphazene compound of the aspect 1.

The oligophosphazene compound of the aspect 2 may include a single kind of constituent unit U1 having the same sulfur-containing ring containing a phosphorus atom of the phosphazene skeleton as its constituent atom, or more than one kind of constituent unit U1 each having a different sulfur-containing ring. Also, the oligophosphazene compound of the aspect 2 may include a single kind of constituent unit U2 having the same structure, or more than one kind of constituent unit U2 each having a different structure.

In the scope of the oligophosphazene compounds of the present invention, possible tautomers and structural isomers thereof are included with respect to any form described above. Examples of the tautomers include those in which the hydrogen atom of $X^1$ rearranges to a nitrogen atom of the phosphazene skeleton when $X^1$ of the structural unit U1 is an amino group. Further, examples of the structural isomer include those formed by rearrangement in which one end of the $(CH_2)_k$ chain of a constituent unit U1 rearranges to a nitrogen atom of the phosphazene skeleton from the sulfur atom or $X^1$, and those formed by rearrangement in which $R^1$ or $R^2$ of a constituent unit U2 rearranges to a nitrogen atom in the phosphazene skeleton from $X^2$ or $X^3$.

The oligophosphazene compound of the present invention is preferably a cyclic oligophosphazene compound which includes both the constituent unit U1 and the constituent unit U2 and has a total content m+n of these constituent units of 3 or 4, that is, cyclotriphosphazene (trimer) or cyclotetraphosphazene (tetramer) composed of both the constituent unit U1 and the constituent unit U2.

Specific examples of preferred oligophosphazene compound of the present invention include 3,3,5,5-tetraamino-1,1-(epithioethanoimino)cyclotriphosphazene, 3,3,5,5-tetraamino-1,1-(epithiopropanoimino)cyclotriphosphazene, 3,3,5,5-tetraamino-1,1-(N-methylepithioethanoimino)cyclotriphosphazene, 3,3,5,5-tetraamino-1,1-(N-methylepithiopropanoimino)cyclotriphosphazene, cis-5,5-diamino-1,1:3,3-bis(epithioethanoimino)cyclotriphosphazene, trans-5,5-diamino-1,1:3,3-bis(epithioethanoimino)cyclotriphosphazene, cis-5,5-diamino-1,1:3,3-bis(epithiopropanoimino)cyclotriphosphazene, trans-5,5-diamino-1,1:3,3-bis(epithiopropanoimino)cyclotriphosphazene, cis-5,5-diamino-1,1:3,3-bis(N-methylepithioethanoimino)cyclotriphosphazene, trans-5,5-diamino-1,1:3,3-bis(N-methylepithioethanoimino)cyclotriphosphazene, cis-5,5-diamino-1,1:3,3-bis(N-methylepithiopropanoimino)cyclotriphosphazene, trans-5,5-diamino-1,1:3,3-bis(N-methylepithiopropanoimino)cyclotriphosphazene, 3,3,5,5-tetrakis(methylamino)-1,1-(epithioethanoimino)cyclotriphosphazene, 3,3,5,5-tetrakis(methylamino)-1,1-(epithiopropanoimino)cyclotriphosphazene, 3,3,5,5-tetrakis(methylamino)-1,1-(N-methylepithioethanoimino)cyclotriphosphazene, 3,3,5,5-tetrakis(methylamino)-1,1-(N-methylepithiopropanoimino)cyclotriphosphazene, cis-5,5-bis(methylamino)-1,1:3,3-bis(epithioethanoimino)cyclotriphosphazene, trans-5,5-bis(methylamino)-1,1:3,3-bis(epithioethanoimino)cyclotriphosphazene, cis-5,5-bis(methylamino)-1,1:3,3-bis(epithiopropanoimino)cyclotriphosphazene, trans-5,5-bis(methylamino)-1,1:3,3-bis(epithiopropanoimino)cyclotriphosphazene, cis-5,5-bis(methylamino)-1,1:3,3-bis(N-methylepithioethanoimino)cyclotriphosphazene, trans-5,5-bis(methylamino)-1,1:3,3-bis(N-methylepithioethanoimino)cyclotriphosphazene, cis-5,5-bis(methylamino)-1,1:3,3-bis(N-methylepithiopropanoimino)cyclotriphosphazene, trans-5,5-bis(methylamino)-1,1:3,3-bis(N-methylepithiopropanoimino)cyclotriphosphazene, 3,3,5,5-tetrakis(ethylamino)-1,1-(epithioethanoimino)cyclotriphosphazene, 3,3,5,5-tetrakis(ethylamino)-1,1-(epithiopropanoimino)cyclotriphosphazene, 3,3,5,5-tetrakis(ethylamino)-1,1-(N-methylepithioethanoimino)cyclotriphosphazene, 3,3,5,5-tetrakis(ethylamino)-1,1-(N-methylepithiopropanoimino)cyclotriphosphazene, cis-5,5-bis(ethylamino)-1,1:3,3-bis(epithioethanoimino)cyclotriphosphazene, trans-5,5-bis(ethylamino)-1,1:3,3-bis(epithioethanoimino)cyclotriphosphazene, cis-5,5-bis(ethylamino)-1,1:3,3-bis(epithiopropanoimino)cyclotriphosphazene, trans-5,5-bis(ethylamino)-1,1:3,3-bis(epithiopropanoimino)cyclotriphosphazene, cis-5,5-bis(ethylamino)-1,1:3,3-bis(N-methylepithioethanoimino)cyclotriphosphazene, trans-5,5-bis(ethylamino)-1,1:3,3-bis(N-methylepithioethanoimino)cyclotriphosphazene, cis-5,5-bis(ethylamino)-1,1:3,3-bis(N-methylepithiopropanoimino)cyclotriphosphazene, trans-5,5-bis(ethylamino)-1,1:3,3-bis(N-methylepithiopropanoimino)cyclotriphosphazene, 3,3,5,5-tetrakis(methylthio)-1,1-(epithioethanoimino)cyclotriphosphazene, 3,3,5,5-tetrakis(methylthio)-1,1-(epithiopropanoimino)cyclotriphosphazene, 3,3,5,5-tetrakis(methylthio)-1,1-(N-methylepithioethanoimino)cyclotriphosphazene, 3,3,5,5-tetrakis(methylthio)-1,1-(N-methylepithiopropanoimino)cyclotriphosphazene, cis-5,5-bis(methylthio)-1,1:3,3-bis(epithioethanoimino)cyclotriphosphazene, trans-5,5-bis(methylthio)-1,1:3,3-bis(epithioethanoimino)cyclotriphosphazene, cis-5,5-bis(methylthio)-1,1:3,3-bis(epithiopropanoimino)cyclotriphosphazene, trans-5,5-bis(methylthio)-1,1:3,3-bis(epithiopropanoimino)cyclotriphosphazene, cis-5,5-bis(methylthio)-1,1:3,3-bis(N-methylepithioethanoimino)cyclotriphosphazene, trans-5,5-bis(methylthio)-1,1:3,3-bis(N-methylepithioethanoimino)cyclotriphosphazene, cis-5,5-bis(methylthio)-1,1:3,3-bis(N-methylepithiopropanoimino)cyclotriphosphazene, trans-5,5-bis(methylthio)-1,1:3,3-bis(N-methylepithiopropanoimino)cyclotriphosphazene, 3,3,5,5-tetrakis[(methylthio)methylamino]-1,1-(epithioethanoimino)cyclotriphosphazene, 3,3,5,5-tetrakis[(methylthio)methylamino]-1,1-(epithiopropanoimino)cyclotriphosphazene, 3,3,5,5-tetrakis[(methylthio)methylamino]-1,1-(N-methylepithioethanoimino)cyclotriphosphazene, 3,3,5,5-tetrakis[(methylthio)methylamino]-1,1-(N-methylepithiopropanoimino)cyclotriphosphazene, cis-5,5-bis[(methylthio)methylamino]-1,1:3,3-bis(epithioethanoimino)cyclotriphosphazene, trans-5,5-bis[(methylthio)methylamino]-1,1:3,3-bis(epithioethanoimino)cyclotriphosphazene, cis-5,5-bis[(methylthio)methylamino]-1,1:3,3-bis(epithiopropanoimino)cyclotriphosphazene, trans-5,5-bis[(methylthio)methylamino]-1,1:3,3-bis(epithiopropanoimino)cyclotriphosphazene, cis-5,5-bis[(methylthio)methylamino]-1,1:3,3-bis(N-methylepithioethanoimino)cyclotriphosphazene, trans-5,5-bis[(methylthio)methylamino]-1,1:3,3-bis(N-methylepithioethanoimino)cyclotriphosphazene, cis-5,5-bis[(methylthio)methylamino]-1,1:3,3-bis(N-methylepithiopropanoimino)cyclotriphosphazene, trans-5,5-bis[(methylthio)methylamino]-1,1:3,3-bis(N-methylepithiopropanoimino)cyclotriphosphazene, 3,3,5,5-tetrakis[2-(methylthio)ethylamino]-1,1-(epithioethanoimino)cyclotriphosphazene, 3,3,5,5-tetrakis[2-(methylthio)ethylamino]-1,1-(epithiopropanoimino)cyclotriphosphazene, 3,3,5,5-tetrakis[2-(methylthio)ethylamino]-1,1-(N-methylepithioethanoimino)cyclotriphosphazene, 3,3,5,5-tetrakis[2-(methylthio)ethylamino]-1,1-(N-methylepithiopropanoimino)cyclotriphosphazene, cis-5,5-bis[2-(methylthio)ethylamino]-1,1:3,3-bis(epithioethanoimino)cyclotriphosphazene, trans-5,5-bis[2-(methylthio)ethylamino]-1,1:3,3-bis(epithioethanoimino)cyclotriphosphazene, cis-5,5-bis[2-(methylthio)ethylamino]-1,1:3,3-bis(epithiopropanoimino)cyclotriphosphazene, trans-5,5-bis[2-(methylthio)ethylamino]-1,1:3,3-bis(epithiopropanoimino)cyclotriphosphazene, cis-5,5-bis[2-(methylthio)ethylamino]-1,1:3,3-bis(N-methylepithioethanoimino)cyclotriphosphazene, trans-5,5-bis[2-(methylthio)ethylamino]-1,1:3,3-bis(N-methylepithioethanoimino)cyclotriphosphazene, cis-5,5-bis[2-(methylthio)ethylamino]-1,1:3,3-bis(N-methylepithiopropanoimino)cyclotriphosphazene, trans-5,5-bis[2-(methylthio)ethylamino]-1,1:3,3-bis(N-methylepithiopropanoimino)cyclotriphosphazene; tautomers formed by rearrangement of a hydrogen atom between an amino group and a nitrogen atom in the phosphazene skeleton in these phosphazene compounds; structural isomers formed by rearrangement in which one end of the $(CH_2)_k$ chain of a constituent unit U1 rearranges to a nitrogen atom of the phosphazene skeleton from the sulfur atom or $X^1$ in these phosphazene compound, and structural isomers formed by rearrangement in which $R^1$ or $R^2$ of a constituent unit U2 rearranges to a nitrogen atom in the phosphazene skeleton from $X^2$ or $X^3$.

Specific examples of the structural isomers include 6-imino-5-methyl-6-methylamino-2,2:4.4-bis(epithioethanoimino)cyclotriphosphaza-1,3-diene, 6-imino-4,4-bis(methylamino)-6,5-(epithioethano)-2,2-(epithioethanoimino)cyclotriphosphaza-1,3-diene, 4,4-bis(methylamino)-6-thioxo-6,5-(epiminoethano)-2,2-(epithioethanoimino)cyclotriphosphaza-1-3-diene, 6-imino-2,2-bis(methylamino)-6,5-(epithioethano)-4,4-(epithioethanoimino)cyclotriphosphaza-1,3-diene, 2,2-bis(methylamino)-6-thioxo-6,5-(epiminoethano)-4,4-(epithioethanoimino)cyclotriphosphaza-1,3-diene, 4,6-diimino-5-methyl-6-methylamino-4,3-(epithioethano)-2,2-(epithioethanoimino)cyclotriphophosphaza-1-ene, 6-imino-5-methyl-6-methylamino-4-thioxo-4,3-(epiminoethano)-2,2-(epithioethanoimino)cyclotriphosphaza-1-ene, 4,6-diimino-3-methyl-4-methylamino-6,5-(epithioethano)-2,2-(epithioethanoimino)cyclotriphophosphaza-1-ene, 4-imino-3-methyl-4-methylamino-6-thioxo-6,5-(epiminoethano)-2,2-(epithioethanoimino)cyclotriphophosphaza-1-ene, 4,6-diimino-2,2-bis(methylamino)-4,3:6,5-bis(epithioethano)cyclotriphophosphaza-1-ene, 4-imino-2,2-bis(methylamino)-6-thioxo-6,5-(epiminoethano)-4,3-(epithioethano)cyclotriphophosphaza-1-ene, 6-imino-2,2-bis(methylamino)-4-thioxo-4,3-(epiminoethano)-6,5-(epithioethano)cyclotriphophosphaza-1-ene, 2,2-bis(methylamino)-4,6-dithioxo-4,3;6,5-bis(epiminoethano)cyclotriphophosphaza-1-ene, 2,4,6-triimino-5-methyl-6-methylamino-2,1:4,3-bis(epithioethano)cyclotriphosphazane, 4,6-diimino-5-methyl-2-thioxo-2,1-(epiminoimino)-4,3-(epithioethano)cyclotriphosphazane, 2,6-diimino-5-methyl-4-thioxo-4,3-(epiminoimino)-2,1-(epithioethano)cyclotriphosphazane and 6-imino-5-methyl-2,4-dithioxo-2,1:4,3-bis(epiminoimino)cyclotriphosphazane derived from 5,5-diamino-1,1:3,3-bis(epithioethanoimino)cyclotriphosphazen.

Among these specific examples, particularly preferred oligophosphazene compounds of the present invention are cis-5,5-diamino-1,1:3,3-bis(epithioethanoimino)cyclotriphosphazene, trans-5,5-diamino-1,1:3,3-bis(epithioethanoimino)cyclotriphosphazene, cis-5,5-diamino-1,1:3,3-bis(epithiopropanoimino)cyclotriphosphazene, trans-5,5-diamino-1,1:3,3-bis(epithiopropanoimino)cyclotriphosphazene, cis-5,5-diamino-1,1:3,3-bis(N-methylepithioethanoimino)cyclotriphosphazene, trans-5,5-diamino-1,1:3,3-bis(N-methylepithioethanoimino)cyclotriphosphazene, cis-5,5-bis(methylamino)-1,1:3,3-bis(epithioethanoimino)cyclotriphosphazene, trans-5,5-(methylamino)-1,1:3,3-bis(epithioethanoimino)cyclotriphosphazene, cis-5,5-bis(methylamino)-1,1:3,3-bis(epithiopropanoimino)cyclotriphosphazene, trans-5,5-(methylamino)-1,1:3,3-bis(epithioronoimino)cyclotriphosphazene, cis-5,5-bis(methylamino)-1,1:3,3-bis(N-methylepithioethanoimino)cyclotriphosphazene, trans-5,5-bis(methylamino)-1,1:3,3-bis(N-methylepithioethanoimino)cyclotriphosphazene, cis-5,5-bis(ethylamino)-1,1:3,3-bis(epithioethanoimino)cyclotriphosphazene, trans-5,5-bis(ethylamino)-1,1:3,3-bis(epithioethanoimino)cyclotriphosphazene, cis-5,5-bis(ethylamino)-1,1:3,3-bis(epithiopropanoimino)cyclotriphosphazene, trans-5,5-bis(ethylamino)-1,1:3,3-bis(epithiopropanoimino)cyclotriphosphazene, cis-5,5-bis(ethylamino)-1,1:3,3-bis(N-methylepithioethanoimino)cyclotriphosphazene, trans-5,5-bis(ethylamino)-1,1:3,3-bis(N-methylepithioethanoimino)cyclotriphosphazene, cis-5,5-bis(methylthio)-1,1:3,3-bis(epithioethanoimino)cyclotriphosphazene, trans-5,5-(methylthio)-1,1:3,3-bis(epithioethanoimino)cyclotriphosphazene, cis-5,5-bis(methylthio)-1,1:3,3-bis(epithiopropanoimino)cyclotriphosphazene, trans-5,5-(methylthio)-1,1:3,3-bis(epithiopropanoimino)cyclotriphosphazene, cis-5,5-bis(methylthio)-1,1:3,3-bis(N-methylepithioethanoimino)cyclotriphosphazene, trans-5,5-bis(methylthio)-1,1:3,3-bis(N-methylepithioethanoimino)cyclotriphosphazene, cis-5,5-bis[2-(methylthio)ethylamino]-1,1:3,3-bis(epithioethanoimino)cyclotriphosphazene, trans-5,5-bis[2-(methylthio)ethylamino]-1,1:3,3-bis(epithioethanoimino)cyclotriphosphazene, cis-5,5-bis[2-(methylthio)ethylamino]-1,1:3,3-bis(epithiopropanoimino)cyclotriphosphazene, trans-5,5-bis[2-(methylthio)ethylamino]-1,1:3,3-bis(epithiopropanoimino)cyclotriphosphazene, cis-5,5-bis[2-(methylthio)ethylamino]-1,1:3,3-bis(N-methylepithioethanoimino)cyclotriphosphazene, trans-5,5-bis[2-(methylthio)ethylamino]-1,1:3,3-bis(N-methylepithioethanoimino)cyclotriphosphazene; tautomers formed by rearrangement of a hydrogen atom between an amino group and a nitrogen atom in the phosphazene skeleton in these phosphazene compounds; structural isomers formed by rearrangement in which one end of the $(CH_2)_k$ chain of a constituent unit U1 rearranges to a nitrogen atom of the phosphazene skeleton from the sulfur atom or $X^1$ in these phosphazene compounds, and structural isomers formed by rearrangement in which $R^1$ or $R^2$ of a constituent unit U2 rearranges to a nitrogen atom in the phosphazene skeleton from $X^2$ or $X^3$.

Particularly preferred oligophosphazene compounds of the present invention are cis-5,5-diamino-1,1:3,3-bis(epithioethanoimino)cyclotriphosphazene, trans-5,5-diamino-1,1:3,3-bis(epithioethanoimino)cyclotriphosphazene, cis-5,5-bis(methylamino)-1,1:3,3-bis(epithioethanoimino)cyclotriphosphazene, trans-5,5-bis(methylamino)-1,1:3,3-bis(epithioethanoimino)cyclotriphosphazene, cis-5,5-bis(ethylamino)-1,1:3,3-bis(epithioethanoimino)cyclotriphosphazene, trans-5,5-bis(ethylamino)-1,1:3,3-bis(epithioethanoimino)cyclotriphosphazene, cis-5,5-bis(methylthio)-1,1:3,3-bis(epithioethanoimino)cyclotriphosphazene, trans-5,5-bis(methylthio)-1,1:3,3-bis(epithioethanoimino)cyclotriphosphazene, cis-5,5-bis[2-(methylthio)ethylamino]-1,1:3,3-bis(epithioethanoimino)cyclotriphosphazene, trans-5,5-bis[2-(methylthio)ethylamino]-1,1:3,3-bis(epithioethanoimino)cyclotriphosphazene; and tautomers formed by rearrangement of a hydrogen atom between an amino group and a nitrogen atom in the phosphazene skeleton in these phosphazene compounds.

A mixture of more than one kind of phosphazene compound selected from the above specific examples is also included as a preferred oligophosphazene compound of the present invention.

Next, the method for producing an oligophosphazene compound of the present invention will be described.

First, a halogenated oligophosphazene compound including a phosphonitrile dihalide unit represented by the following general formula (IV) is prepared.

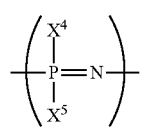

In the general formula (IV), $X^4$ and $X^5$ each represents a halogen atom. This halogen atom is usually fluorine, chlorine or bromine, and is preferably fluorine or chlorine, and particularly preferably chlorine. $X^4$ and $X^5$ may be the same or different.

The halogenated oligophosphazene compound including the phosphonitrile dihalide unit represented by the general formula (IV) can be appropriately selected according to the kind of objective oligophosphazene compound of the present invention. That is, a halogenated oligophosphazene compound in which the phosphonitrile dihalide units are circularly linked is used for the production of a cyclic oligophosphazene compound of the present invention. Similarly, a halogenated oligophosphazene compound in which the phosphonitrile dihalide units are linearly linked is used for the production of a linear oligophosphazene compound of the present invention. Furthermore, a mixture of a halogenated cyclic oligophosphazene compound and a halogenated linear oligophosphazene compound is used for the production of a mixture of the cyclic oligophosphazene compound and the linear oligophosphazene compound.

The linear halogenated oligophosphazene compound used herein is, for example, a compound in which its terminal structures at the phosphorus atom side and the nitrogen atom side are as follows.
The terminal structure at the phosphorus atom:

The terminal structure at the nitrogen atom:

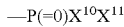

In the formula, $X^9$, $X^{10}$ and $X^{11}$ represent a halogen atom. $X^9$, $X^{10}$ and $X^{11}$ usually represent fluorine, chlorine or bromine, preferably fluorine or chlorine, and particularly preferably chlorine.

In the halogenated oligophosphazene compound, the number t of the phosphonitrile dihalide unit is usually an integer of 3 to 14 and can be selected according to the oligophosphazene compound to be produced. The halogenated oligophosphazene compound may be a mixture of several kinds of compound each having a different number t.

Examples of the preferred halogenated oligophosphazene compound to be used herein include hexachlorocyclotriphosphazene (trimer having t of 3), octachlorocyclotetraphosphazene (tetramer having t of 4), decachlorocyclopentaphosphazene (pentamer having t of 5), dodecachlorocyclohexaphosphazene (hexamer having t of 6), and a mixture of hexachlorocyclotriphosphazene and octachlorocyclotetraphosphazene.

Both the halogenated oligophosphazene compound in which the phosphonitrile dihalide unit is circularly linked and the halogenated oligophosphazene compound in which the phosphonitrile dihalide unit is linearly linked are known compounds. They can be produced according to known synthesis methods and can be purchased from commercial sources.

Next, at least one step of the following steps (a-1) and (a-2) is applied to the above halogenated oligophosphazene compound thereby converting halogen atoms of the halogenated oligophosphazene compound into predetermined sulfur-containing rings (hereinafter this step is referred to as "step A").
Step (a-1)
A step of nucleophilically substituting halogen atoms of the phosphonitrile dihalide unit in an halogenated oligophosphazene compound, using at least one kind of compound among the group of difunctional alkylthiol compounds having a group selected from the group consisting of an amino group, a hydroxyl group and a mercapto (thiol) group in the presence of a base capable of scavenging a hydrogen halide.

The difunctional alkylthiol compound having an amino group, which can be used in this step, is a compound having two functional groups of an amino group and a thiol group, and examples thereof include mercaptomethylamine, N-methylmercaptomethylamine, 2-mercaptoethylamine, N-methyl-2-mercaptoethylamine, 3-mercaptopropylamine, N-methyl-3-mercaptopropylamine, 4-mercaptobutylamine and N-methyl-4-mercaptobutylamine. Among these compounds, 2-mercaptoethylamine, N-methyl-2-mercaptoethylamine, 3-mercaptopropylamine and N-methyl-3-mercaptopropylamine are preferred, and 2-mercaptoethylamine and 3-mercaptopropylamine are particularly preferred. The difunctional alkylthiol compound of this type may form a salt such as hydrochloride. The difunctional alkylthiol compound of this type may be used alone, or more than one kind of them can be used in combination.

The difunctional alkylthiol compound having a hydroxyl group, which can be used in this step, is a compound having two functional groups of a hydroxyl group and a thiol group, and examples thereof include mercaptomethanol, 2-mercaptoethanol, 3-mercaptopropanol and 4-mercaptobutanol. Among these compounds, 2-mercaptoethanol and 3-mercaptopropanol are preferred, and 2-mercaptoethanol is particularly preferred. The difunctional alkylthiol compound of this type may be used alone, or more than one kind of them can be used in combination.

The difunctional alkylthiol compound having a mercapto group, which can be used in this step, is a compound having two thiol groups (mercapto groups), and examples thereof include methanedithiol, 1,2-ethanedithiol, 1,3-propanedithiol and 1,4-butanedithiol. Among these compounds, 1,2-ethanedithiol and 1,3-propanedithiol are preferred, and 1,2-ethanedithiol is particularly preferred. The difunctional alkylthiol compound of this type may be used alone, or more than one kind of them can be used in combination.

The base which can be used in this step for the scavenging of a hydrogen halide is not particularly limited. Preferred examples thereof include aliphatic amines such as trimethylamine, triethylamine and diisopropylethylamine; aromatic amines such as dimethylaniline, diethylaniline, diisopropylaniline, pyridine, 4,4-dimethylaminopyridine, 4,4-diethylaminopyridine and 4-diisopropylaminopyridine; alkali metal carbonates such as sodium carbonate, potassium carbonate, sodium hydrogencarbobonate and potassium hydrogencarbonate; and alkali metal hydroxides such as sodium hydroxide, potassium hydroxide and lithium hydroxide. Among these, triethylamine, pyridine and alkali metal hydroxides such as potassium hydroxide are particularly preferred.

Among the difunctional alkylthiol compounds used in this step, a difunctional alkylthiol compound having an amino group can be used as the base capable of scavenging a hydrogen halide.

The amount of the base capable of scavenging a hydrogen halide used is not particularly limited, and is preferably set to be within a range from 1 to 4 equivalents, and particularly preferably from 1 to 2 equivalents, with respect to the halogen atoms to be substituted in the halogenated oligophosphazene compound used in the step (a-1).

In this step, it is preferred to react the halogenated oligophosphazene compound and the difunctional alkylthiol compound in an organic solvent containing the base capable of scavenging a hydrogen halide. Examples of the organic solvent, which can be used herein, include aprotic solvents such as acetonitrile, dichloromethane, chloroform, diethylether, tetrahydrofuran, dioxane, benzene, toluene and chlorobenzene. Acetonitrile, dichloromethane, chloroform, diethylether, tetrahydrofuran and dioxane are preferably used, and acetonitrile, dichloromethane, chloroform and dioxane are particularly preferably used.

The reaction temperature can be appropriately set according to the reactivity between the halogenated oligophosphazene compound and the difunctional alkylthiol compound and is not particularly specified, but is preferably within a range from −80 to 150° C., and particularly preferably from −20 to 30° C.

Step (a-2)

A step of nucleophilically substituting halogen atoms of the phosphonitrile dihalide unit constituting a halogenated oligophosphazene compound using a metal salt of at least one kind of compound among the group of the difunctional alkylthiol compounds having either a hydroxyl group or a mercapto group.

The metal salt of the difunctional alkylthiol compound having a hydroxyl group, which can be used in this step, is an alcolate, thiorate or alcolate/thiorate in which hydrogen atoms of one or both of the hydroxyl group and the thiol group of the difunctional alkylthiol compound having a hydroxyl group described in the step (a-1) are substituted with a metal atom, preferably an alkali metal atom. The metal salt of the difunctional alkylthiol compound having a mercapto group, which can be used in this step, is a thiorate in which hydrogen atoms of one or both of the thiol (mercapto) groups of the difunctional alkylthiol compound having a mercapto group described in the step (a-1) are substituted with a metal atom, preferably an alkali metal atom.

Such a metal salt can be prepared by reacting the difunctional alkylthiol compound having either a hydroxyl group or a mercapto group with a metal or a metal compound, for example, an alkali metal such as metallic lithium, metallic sodium, metallic potassium, lithium hydride, sodium hydride and potassium hydride, or an organometal compound such as n-butyl lithium, t-butyl lithium and potassium t-butyl oxide.

In this case, the ratio of the difunctional alkylthiol compound having either a hydroxyl group or a mercapto group and the metal or metal compound is not particularly limited. It is preferred to set the amount of the metal or metal compound to be within a range from 0.5 to 4 equivalents, and particularly preferably from 1 to 2 equivalents, based on the difunctional alkylthiol compound having either a hydroxyl group or a mercapto group.

In this step, it is preferred to react the halogenated oligophosphazene compound and a metal salt of the difunctional alkylthiol compound in an organic solvent. The organic solvent, which can be used herein, is the same as that listed in the step (a-1). Acetonitrile, chlorobenzene, diethylether, tetrahydrofuran and dioxane are preferably used, and acetonitrile and tetrahydrofuran are more preferably used.

The reaction temperature can be appropriately set according to the reactivity between the halogenated oligophosphazene compound and a metal salt of the difunctional alkylthiol compound and is not particularly specified, but is preferably within a range from −80 to 150° C., and particularly preferably from −20 to 30° C.

In the step A, only the step (a-1) may be carried out, or only the step (a-2) may be carried out. The step (a-1) and the step (a-2) can also be used in combination. When both steps are used in combination, a portion of halogen atoms of the halogenated oligophosphazene compound is converted into a predetermined sulfur-containing ring by applying the step (a-1) to the halogenated oligophosphazene compound, and then by applying the step (a-2) to the thus obtained phosphazene compound, all or a portion of the remained halogen atoms is/are converted into a predetermined sulfur-containing ring. The order of the step (a-1) and the step (a-2) can be changed.

When the oligophosphazene compound of the aspect 1 is produced, all halogen atoms of the halogenated oligophosphazene compound are converted into predetermined sulfur-containing rings in the step A. When the oligophosphazene compound of the aspect 1 is produced only by the step (a-1) or step (a-2), the amount of the difunctional alkylthiol compound or the metal salt of the difunctional alkylthiol compound used is preferably set to be within a range from 0.5 to 2 equivalents, and particularly preferably from 0.5 to 1 equivalent, based on the halogen atoms of the halogenated oligophosphazene compound.

In the case of employing the step (a-1), when the difunctional alkylthiol compound having an amino group is used as the substituent and at the same time is also used as the base capable of scavenging a hydrogen halide, the amount of the difunctional alkylthiol compound having an amino group is set to be the amount in which a predetermined amount used as the base is added to the above-mentioned amount used as the substituent.

When the oligophosphazene compound of the aspect 1 is produced by using the step (a-1) and the step (a-2) in combination, the amount of the difunctional alkylthiol compound is preferably set to be within a range from 0.5 to 2 equivalents, and particularly preferably from 0.5 to 1 equivalent, based on the halogen atoms to be substituted in the halogenated oligophosphazene compound used in the step (a-1). The amount of the metal salt of the difunctional alkylthiol compound is preferably set to be within a range from 0.5 to 2 equivalents, and particularly preferably from 0.5 to 1 equivalent, based on the halogen atoms to be substituted in the halogenated oligophosphazene compound used in the step (a-2).

Here, in the step (a-1), when the difunctional alkylthiol compound having an amino group is used as the substituent and at the same time is also used as the base capable of scavenging a hydrogen halide, the amount of the difunctional alkylthiol compound having an amino group is set to be the amount in which a predetermined amount used as the base is added to the above-mentioned amount used as the substituent.

When the oligophosphazene compound of the aspect 2 is produced, a portion of halogen atoms of the halogenated oligophosphazene compound is converted into predetermined sulfur-containing rings in the step A and then all of the remained halogen atoms are converted into predetermined substituents by applying at least one step of the steps (b-1) and (b-2) described below to the thus obtained partially substituted halogenated oligophosphazene compound (hereinafter the latter step is referred to as "step B").

In this case, in the step A, the amount of the difunctional alkylthiol compound or the metal salt of the difunctional alkylthiol compound used in the step (a-1) or step (a-2) is adjusted, or the amount of the difunctional alkylthiol compound used in the step (a-1) and the amount of the metal salt of the difunctional alkylthiol compound used in the step (a-2) are adjusted respectively, so that the number m of the constituent unit U1 included in the partially substituted halogenated oligophosphazene compound is adjusted within the range described above.

When the oligophosphazene compound of the aspect 2 is produced by carrying out the step B after the step A through the step (a-1) or step (a-2), the amount of the difunctional alkylthiol compound used in the step (a-1) or the metal salt of the difunctional alkylthiol compound used in the step (a-2) is preferably set to be within a range from 0.5 to 2 equivalents, and particularly preferably from 0.5 to 1 equivalent, based on the halogen atoms to be substituted in the halogenated oligophosphazene compound used in the step A. When the oligophosphazene compound of the aspect 2 is produced by carrying out the step B after the step A through both the steps (a-1) and (a-2), the amount of the difunctional alkylthiol compound used is preferably set to be within a range from 0.5 to 2 equivalents, and particularly preferably from 0.5 to 1 equivalent, based on the halogen atoms to be substituted in the halogenated oligophosphazene compound used in the step (a-1). The amount of the metal salt of the difunctional alkylthiol compound used is preferably set to be within a range from 0.5 to 2 equivalents, and particularly preferably from 0.5 to 1 equivalent, based on the halogen atoms to be substituted in the halogenated oligophosphazene compound used in the step (a-2).

In the step (a-1), when the difunctional alkylthiol compound having an amino group is used as the substituent and at the same time is also used as the base capable of scavenging a hydrogen halide, the amount of the difunctional alkylthiol compound having an amino group is set to be the amount in which a predetermined amount used as the base is added to the above-mentioned amount used as the substituent.

Step (b-1)

A step of nucleophilically substituting halogen atoms remained in a partially halogenated oligophosphazene compound with at least one kind of compound selected from the group consisting of a monofunctional alkyl compound having a group selected from the group consisting of an amino group, a hydroxyl group and a mercapto group, a monofunctional thioalkyl compound having a group selected from the group consisting of an amino group, a hydroxyl group and a mercapto group, a monofunctional phenyl compound having a group selected from the group consisting of an amino group, a hydroxyl group and a mercapto group and ammonia in the presence of a base capable of scavenging a hydrogen halide.

As the monofunctional alkyl compound having an amino group which can be used in this step, for example, methylamine, ethylamine and the like are used. In this alkyl compound, an amino group may form a salt such as hydrochloride. As the monofunctional alkyl compound having a hydroxyl group, for example, methanol, ethanol, methoxymethanol, ethoxymethanol, 2-(methoxy)ethanol, 2-(ethoxy)ethanol and the like are used. As the monofunctional alkyl compound having a mercapto group, for example, methanethiol, ethanethiol and the like are used. Examples of the monofunctional thioalkyl compound having an amino group include (methylthio)methylamine, 2-(methylthio) ethylamine, (ethylthio)methylamine, 2-(ethylthio)ethylamine, [(methylthio)methylthio]methylamine, 2-[(methylthio)methylthio]ethylamine, [2-(methylthio)ethylthio] methylamine, [(ethylthio)methylthio]methylamine, 2-[2-(methylthio)ethylthio]ethylamine, 2-[(ethylthio)methylthio] ethylamine, [2-(ethylthio)ethylthio]methylamine, 2-[2-(ethylthio)ethylthio]ethylamine, dimethylamine, ethylmethylamine, N-methyl(methylthio)methylamine, N-methyl-2-(methylthio)ethylamine, N-methyl(ethylthio) methylamine, N-methyl-2-(ethylthio)ethylamine, N-methyl [(methylthio)methylthio]methylamine, N-methyl-2-[(methylthio)methylthio]ethylamine, N-methyl-[2-(methylthio) ethylthio]methylamine, N-methyl-2-[(ethylthio)methylthio] methylamine, N-methyl-2-[2-(methylthio)ethylthio] ethylamine, N-methyl-2-[(ethylthio)methylthio]ethylamine, N-methyl-[2-(ethylthio)ethylthio]methylamine and N-methyl-2-[2-(ethylthio) ethylthio]ethylamine. In this thioalkyl compound, the amino group may form a salt such as hydrochloride. As the monofunctional thioalkyl compound having a hydroxyl group, for example, there can be used (methylthio) methanol, 2-(methylthio)ethanol, (ethylthio)methanol, 2-(ethylthio)ethanol, [(methylthio)methylthio]methanol, 2-[(methylthio)methylthio]ethanol, [2-(methylthio)etherthio]methanol, [(etherthio)methylthio]methanol, 2-[2-(methylthio)ethylthio]ethanol, 2-[(ethylthio)methylthio]ethanol, [2-(ethylthio)ethylthio]methanol, 2-[2-(ethylthio)ethylthio] ethanol and the like. As the monofunctional thioalkyl compound having a mercapto group, for example, (methylthio) methanethiol, (ethylthio)methanethiol, 2-(methylthio) ethanethiol, 2-(ethylthio)ethanethiol and the like are used. As the monofunctional phenyl compound having an amino group, for example, aniline and the like are used. In this phenyl compound, the amino group may form a salt such as hydrochloride. As the monofunctional phenyl compound having a hydroxyl group, for example, phenol and the like are used. As the monofunctional phenyl compound having a mercapto group, for example, thiophenol is used.

Examples of the preferred compounds used in this step include ammonia, methylamine, 2-(methylthio)ethylamine, 2-[(methylthio)methylthio]ethylamine, 2-[2-(methylthio) ethylthio]ethylamine, aniline, methanethiol, 2-(methylthio) ethanethiol, thiophenol and phenol. Among these compounds, ammonia, methylamine, 2-(methylthio)ethylamine, aniline, methanethiol, thiophenol and phenol are particularly preferred.

The base capable of scavenging a hydrogen halide, which can be used in this step, is the same as that described in the step (a-1) Here, among the monofunctional compounds used in this step, a compound having an amino group can be used as the base capable of scavenging a hydrogen halide.

The amount of the base capable of scavenging a hydrogen halide used is not particularly limited, and is preferably set to be within a range from 1 to 4 equivalents, and particularly preferably from 1 to 2 equivalents, based on the halogen atoms to be substituted in the halogenated oligophosphazene compound used in the step (b-1).

This step is preferably carried out in an organic solvent containing the base capable of scavenging a hydrogen halide. Examples of the organic solvent, which can be used herein, include the same as those listed in the step (a-1). Among these, acetonitrile, dichloromethane, chloroform, diethylether, tetrahydrofuran and dioxane are preferably used, and acetonitrile, dichloromethane, chloroform and tetrahydrofuran are particularly preferably used.

The reaction temperature can be appropriately set according to the reactivity between the partially substituted halogenated oligophosphazene compound and the monofunctional compound and is not particularly specified, but is preferably within a range from 0 to 150° C., and particularly preferably from 0 to 70° C.

Step (b-2)

A step of nucleophilically substituting halogen atoms remained in a partially halogenated oligophosphazene compound with at least one kind of compound selected from the group consisting of a metal salt of a monofunctional alkyl compound having either a hydroxyl group or a mercapto group, a metal salt of a monofunctional thioalkyl compound having either a hydroxyl group or a mercapto group and a metal salt of a monofunctional phenyl compound having either a hydroxyl group or a mercapto group.

The metal salt of the monofunctional alkyl compound having a hydroxyl group, which can be used in this step, is an alcolate in which the hydrogen atom of a hydroxyl group of the monofunctional alkyl compound having a hydroxyl group described in the step (b-1) is substituted with a metal atom, preferably an alkali metal atom. The metal salt of the monofunctional alkyl compound having a mercapto group, which can be used in this step, is a thiorate in which the hydrogen atom of a mercapto group of the monofunctional alkyl compound having a mercapto group described in the step (b-1) is substituted with a metal atom, preferably an alkali metal atom.

Such a metal salt can be prepared by reacting a monofunctional alkyl compound having a hydroxyl group or a mercapto group with a metal or a metal compound, for example, an alkali metal such as metallic lithium, metallic sodium, metallic potassium, lithium hydride, sodium hydride and potassium hydride, or an organometal compound such as n-butyl lithium, t-butyl lithium and potassium t-butyl oxide.

In this case, the ratio of the monofunctional alkyl compound having a hydroxyl group or a mercapto group and the metal or metal compound is not particularly limited. It is preferred to set the amount of the metal or metal compound to be within a range from 0.5 to 2 equivalents, and particularly preferably from 0.75 to 1.25 equivalents, based on the monofunctional alkyl compound having a hydroxyl group or a mercapto group.

In this step, it is preferred to react the partially substituted halogenated oligophosphazene compound and the metal salt of the monofunctional alkyl compound in an organic solvent. Here, the organic solvent, which can be used herein, is the same as in the step (b-1). Acetonitrile, chlorobenzene, diethylether, tetrahydrofuran and dioxane are preferably used, and acetonitrile and tetrahydrofuran are more preferably used.

The reaction temperature can be appropriately set according to the reactivity between the partially substituted halogenated oligophosphazene compound and a metal salt of the monofunctional compound and is not particularly specified, but is preferably within a range from 0 to 150° C., and particularly preferably from 0 to 70° C.

In the step B, only the step (b-1) may be carried out, or only the step (b-2) may be carried out. The step (b-1) and the step (b-2) can also be used in combination. When both steps are used in combination, a portion of halogen atoms remained in the partially substituted halogenated oligophosphazene compound is substituted with a predetermined substituent by applying the step (b-1) to the partially substituted halogenated oligophosphazene compound, and then all of the remained halogen atoms are substituted with a predetermined substituent by further applying the step (b-2) to the partially substituted halogenated oligophosphazene compound. The order of the step (b-1) and the step (a-2) can be changed.

When the oligophosphazene compound of the aspect 2 is produced by carrying out the step (b-1) or (b-2), the amount of the monofunctional compound used in the step (b-1) or the metal salt of the monofunctional compound used in the step (b-2) is preferably set to be within a range from 1 to 4 equivalents, and particularly preferably from 1 to 2 equivalents, based on the halogen atoms remained in the partially substituted halogenated oligophosphazene compound. When the oligophosphazene compound of the aspect 2 is produced by carrying out the step B through both the steps (b-1) and (b-2), the amount of the monofunctional compound used is preferably set to be within a range from 1 to 4 equivalents, and particularly preferably from 1 to 2 equivalents, based on the halogen atoms to be substituted in the partially substituted halogenated oligophosphazene compound used in the step (b-1). The amount of the metal salt of the monofunctional compound used is preferably set to be within a range from 1 to 4 equivalents, and particularly preferably from 1 to 2 equivalents, based on the halogen atoms to be substituted in the partially substituted halogenated oligophosphazene compound used in the step (b-2).

Here, in the step (b-1), when the monofunctional compound having an amino group is used as the substituent and at the same time is also used as the base capable of scavenging a hydrogen halide, the amount of the monofunctional compound having an amino group is set to be the amount in which a predetermined amount used as the base is added to the above-mentioned amount used as the substituent.

When the oligophosphazene compound of the aspect 2 is produced, the objective oligophosphazene compound can be produced by producing a partially substituted halogenated oligophosphazene compound in the step A and then carrying out the step B to the partially substituted halogenated oligophosphazene compound, as described above. The objective oligophosphazene compound can also be produced by changing the order of the step A and the step B. That is, the objective oligophosphazene compound can be produced by producing a partially substituted halogenated oligophosphazene compound in the step B and carrying out the step A to the partially substituted halogenated oligophosphazene compound. More specifically, the objective oligophosphazene compound can be produced by converting a portion of halogen atoms of the halogenated oligophosphazene compound in the step B into a predetermined substituted group and applying at least one of the steps (a-1) and (a-2) described above to the thus obtained partially substituted halogenated oligophosphazene compound to convert all of the remained halogen atoms into a predetermined sulfur-containing ring.

In this case, in the step B, the amount of the monofunctional compound or the metal salt of the monofunctional compound used in the step (b-1) or step (b-2) is adjusted, or the amount of the monofunctional compound used in the step (b-1) and the amount of the metal salt of the monofunctional compound used in the step (b-2) are adjusted respectively, so that the number n of the constituent unit U2 included in the partially substituted oligophosphazene compound is adjusted within the range described above.

When the oligophosphazene compound of the aspect 2 is produced by carrying out the step A after the step B through either the step (b-1) or step (b-2), the amount of the monofunctional compound used in the step (b-1) or the metal salt of the monofunctional compound used in the step (b-2) is preferably set to be within a range from 1 to 4 equivalents, and particularly preferably from 1 to 2 equivalents, based on the halogen atoms to be substituted in the halogenated oligophosphazene compound used in the step B. When the oligophosphazene compound of the aspect 2 is produced by carrying out the step A after the step B through both the steps (b-1) and (b-2), the amount of the monofunctional compound used is preferably set to be within a range from 1 to 4 equivalents, and particularly preferably from 1 to 2 equivalents, based on the halogen atoms to be substituted in the halogenated oligophosphazene compound used in the step (b-1). The amount of the metal salt of the monofunctional compound used is preferably set to be within a range from 1 to 4 equivalents, and particularly preferably from 1 to 2 equivalents, based on the halogen atoms of the halogenated oligophosphazene compound to be substituted in the step (b-2).

In the step (b-1), when the monofunctional compound having an amino group is used as the substituent and at the same time is also used as the base capable of scavenging a hydrogen halide, the amount of the monofunctional compound having an amino group is set to be the amount in which a predetermined amount used as the base is added to the above-mentioned amount used as the substituent.

When the oligophosphazene compound of the present invention is heated under an oxygen-free atmosphere, the sulfur-containing ring of the constituent unit U1 opens, and thus polymerization occurs between the molecules. This polymerization progresses by heating a solution in which the oligophosphazene compound is dissolved in an organic solvent, and also progresses by heating the oligophosphazene compound as it is (that is, in the absence of a solvent). The organic solvent used to dissolve the oligophosphazene compound is not particularly limited, and is preferably a non-halogen solvent such as acetonitrile, methanol, ethanol, tetrahydrofuran, dioxane, benzene and toluene. The heating temperature for the polymerization is not particularly limited, and is preferably set to be within a range from 120 to 180° C., and particularly preferably from 150 to 165° C. Upon the polymerization reaction, it is possible to use, as polymerization initiators, acids such as trifluoroacetic acid, fluorosulfonic acid and trifluoromethanesulfonic acid; Lewis acids such as trifluoroboric acid, boron trifluoride and antimony pentachloride; alkali metal hydroxides such as sodium hydroxide and potassium hydroxide; organometallic salts such as lithium alkoxide, sodium alkoxide, potassium alkoxide and sodium naphthalene; and amines such as trimethylamine, triethylamine, dimethylaniline, diethylaniline, pyridine and 4,4-dimethylaminopyridine. When the oligophosphazene compound of the present invention is thermally polymerized in the absence of the solvent, by-products are less likely to be produced and thus a polymer having high transparency suited for optical molding described below can be obtained.

A polymer composed of the oligophosphazene compound of the present invention has a refractive index at a wavelength of 589 nm, which is generally used in the evaluation of optical properties, within a range from 1.55 to 1.65 and also shows high transparency through a wide wavelength range including the infrared region, the visible region and the ultraviolet region. In addition, this polymer has a high Abbe number, which usually shows the magnitude of optical dispersion, within a range from 35 to 45. The Abbe number within the above range is higher than those of common organic polymers composed of hydrogen, oxygen, nitrogen and carbon and is also comparable to those of inorganic materials such as flint glass. Thus the polymer is less likely to cause optical dispersion.

In particular, when the oligophosphazene compound of the present invention is a cyclic oligophosphazene compound, its cyclic phosphazene skeleton is spiro-condensed with the sulfur-containing ring of the constituent unit U1 using the phosphorus atom of the phosphazene skeleton as a spiro atom. Therefore, as described in Inorganic Chemistry 1966, 5, 1016-1020, the sulfur-containing ring easily opens upon heating and thus the polymerization progresses in the absence of a solvent without using a polymerization initiator to form a polymer having remarkably high transparency.

As described above, since the polymer composed of the oligophosphazene compound of the present invention has a high refractive index and high transparency and shows low optical dispersion, it is very useful as materials for various optical moldings, for example, optical lens such as glasses and camera lenses, and light transmission bodies such as retardation films and optical fibers.

Even when the oligophosphazene compound of the present invention is copolymerized with other monomers, a polymer having high transparency suited for optical molding can be obtained. Examples of the other monomers include, but are not limited to, aliphatic compounds or aromatic compounds, each having one or more than one epoxy group, episulfide group, isocyanate group or thioisocyanate group as a polymerizable group. These compounds may contain heteroatoms such as oxygen, nitrogen, and sulfur in the moiety other than that of their polymerizable group.

When the oligophosphazene compound and the other monomers described above are copolymerized, it is possible to use a solvent and an initiator which are used in the above polymerization of the oligophosphazene compound. The heating temperature is not particularly limited and is preferably set to be within a range from 0 to 180° C., and particularly preferably from 80 to 165° C.

Hereinafter, the present invention will be described in more detail by way of Examples.

Example 1

Synthesis of trans-5,5-bis[2-(methylthio)ethylamino]-1,1:3,3-bis(epithioethanoimino)cyclotriphosphazene Hexachlorocyclotriphosphazene (7.650 g, 22.005 mmol), 2-mercaptoethylamine hydrochloride (5.250 g, 46.211 mmol) and dewatered acetonitrile (100 ml) were charged into a 1,000 ml round bottom flask, the atmosphere of which was replaced by dry nitrogen. To this was added triethylamine (6.680 g, 66.015 mmol) under a nitrogen atmosphere over 20 minutes, followed by stirring at 20° C. for 12 hours. Thereafter, a mixed solution of triethylamine (7.348 g, 72.617 mmol) and acetonitrile (50 ml) was further added dropwise over 2 hours, followed by stirring at 20° C. for 12 hours.

Next, the solid (triethylamine hydrochloride) precipitated in the reaction solution was removed by filtration, and triethylamine (4.453 g, 44.010 mmol) and 2-(methylthio)ethylamine (4.815 g, 52.812 mmol) were added to the reaction solution, followed by stirring at 20° C. for 12 hours. The precipitated solid and the solvent were removed and then the crude product was dissolved in dichloromethane (100 ml). The dichloromethane solution was washed once with water (100 ml) and then the solvent was removed. The crude product thus obtained was purified by recrystallization twice from a 50% by weight methanol solution. A mother liquor was recovered and similarly recrystallized twice. Yield of trans-5,5-bis[2-(methylthio)ethylamino]-1,1:3,3-bis(epithioethanoimino)cyclotriphosphazene thus obtained was 31% based on hexachlorocyclotriphosphazene. Analytical results of the obtained cyclotriphosphazene compound were as follows:

$^1$H-NMR (CDCl$_3$) (ppm) 2.10 (s, 6H, SCH$_3$), 2.66 (t, 4H, CH$_2$SCH$_3$), 2.84 (quartet, 2H, NHCH$_2$CH$_2$SCH$_3$), 2.92 (s, 2H, NHCH$_2$CH$_2$SP), 3.13 (m, 4H, NHCH$_2$CH$_2$SCH$_3$), 3.30-3.45 (m, 8H, NHCH$_2$CH$_2$SP)

$^{31}$P-NMR (CDCl$_3$): (ppm) 16.0 (t, 1P), 53.4 (d, 2P)

MS (m/z): 466 MH$^+$

Melting point: 78° C.

Example 2

Synthesis of trans-5,5-bis(methylamino)-1,1:3,3-bis(epithioethanoimino)cyclotriphosphazene Hexachlorocyclotriphosphazene (15.301 g, 44.010 mmol), 2-mercaptoethylamine hydrochloride (10.500 g, 92.421 mmol) and dewatered acetonitrile (200 ml) were charged into a 1,000 ml round bottom flask, the atmosphere of which was replaced by dry nitrogen. To this was added triethylamine (13.360 g, 132.03 mmol) under a nitrogen atmosphere over 20 minutes, followed by stirring at 20° C. for 12 hours. Thereafter, a mixed solution of triethylamine (14.696 g, 145.23 mmol) and acetonitrile (100 ml) was further added dropwise over 2 hours, followed by stirring at 20° C. for 12 hours. The solid (triethylamine hydrochloride) precipitated in the reaction solution was removed by filtration. The reaction solution was transferred to a 1,000 ml round bottom flask equipped with a condenser tube using isopropanol and dry ice as refrigerants and a THF solution (100 ml) containing methylamine in a concentration of 2 M was added, followed by stirring at room temperature for 2 hours.

The precipitate and the solvent were removed from the reaction solution and ethanol (30 ml) was added to the resultant crude product (15 g), followed by shaking at room temperature thereby precipitating powdery crystals. The resultant powder was recovered by filtration and then washed twice with ethanol (30 g) to obtain pure trans-5,5-bis(methylamino)-1,1:3,3-bis(epithioethanoimino)cyclotriphosphazene. The entire ethanol solution used in the washing operation was recovered and ethanol (11 g) was added to the precipitate (11 g) obtained after removing ethanol, followed by shaking at room temperature thereby precipitating powdery crystals. The resultant powder was recovered by filtration and then washed twice with ethanol (11 g), thereby pure trans-5,5-bis(methylamino)-1,1:3,3-bis(epithioethanoimino)cyclotriphosphazene was obtained additionally.

Yield of the entire trans-5,5-bis(methylamino)-1,1:3,3-bis(epithioethanoimino)cyclotriphosphazene obtained by the above operation was 41.6% based on hexachlorocyclotriphosphazene. Analytical results of the obtained cyclotriphosphazene compound were as follows:

$^1$H-NMR(CDCl$_3$): (ppm) 2.21 (s, 2H, NHCH$_3$), 2.58 (quartet, 6H, NHCH$_3$), 2.99 (s, 2H, NHCH$_2$CH$_2$S), 3.25-3.45 (m, 8H, NHCH$_2$CH$_2$S)

$^{31}$P-NMR (CDCl$_3$): (ppm) 19.8 (t, 1P, P (NHCH$_3$)$_2$), 54.0 (d, 2P, P (NHCH$_2$CH$_2$S))

MS (m/z): 346 MH$^+$

Example 3

Polymerization of trans-5,5-bis[2-(methylthio)ethylamino]-1,1:3,3-bis(epithioethanoimino)cyclotriphosphazene A crystal (1.5 g) of trans-5,5-bis[2-(methylthio)ethylamino]-1,1:3,3-bis(epithioethanoimino)cyclotriphosphazene obtained in Example 1 was placed in a mold (12×12×8 mm) made of Teflon and the solvent was removed in a vacuum at 125° C., followed by heating under a normal pressure nitrogen atmosphere at 165° C. for 5.5 hours. As a result, a colorless transparent polymer was obtained. This resultant polymer was a solid at the temperature of 78° C., which is a melting point of trans-5,5-bis[2-(methylthio)ethylamino]-1,1:3,3-bis(epithioethanoimino)cyclotriphosphazene, or higher and was insoluble in an organic solvent.

With respect to the resultant polymer, its refractive index was measured and its Abbe number was determined. The results are shown in Table 1. The refractive index was measured at three wavelengths of 486 nm, 589 nm and 656 nm. Herein, using a refractive index meter PR-2 manufactured by CARL ZEISS JENA, the refractive index was measured at 25° C. by a V block method. The Abbe number is determined by the calculation formula shown below. The larger the value, the smaller the optical dispersion becomes. In the calculation formula, v denotes an Abbe number, and n$_{486}$, n$_{589}$ and n$_{656}$ respectively denote refractive indices at 486 nm, 589 nm and 656 nm.

$$v = \frac{n_{589} - 1}{n_{486} - n_{656}}$$

For comparison, refractive indices and Abbe numbers of two kinds of organic polymer composed of a hydrocarbon having an aromatic ring are shown in Table 1. Since polycarbonate has excellent transparency and exhibits comparatively high refractive index, it is often used as optical materials, for example, materials for an optical lens such as eyeglasses.

TABLE 1

|  | Refractive index | | | Abbe |
|---|---|---|---|---|
|  | 486 nm | 589 nm | 656 nm | number |
| Polymer of Example 3 | 1.6417 | 1.6465 | 1.6583 | 39 |
| Polycarbonate | — | 1.585 | — | 30 |
| Polyvinyl benzoate | — | 1.578 | — | 31 |

According to Table 1, the polymer of Example 3 has a feature that a refractive index at 589 nm and an Abbe number are larger than those of other organic polymers which are considered to have a comparatively high refractive index. The refractive index and the Abbe number of this polymer have never been achieved by common organic polymers composed of hydrogen, carbon, nitrogen and oxygen and, particularly, the Abbe number is a value which is comparable to that of inorganic materials such as flint glass.

The present invention may be embodied in other specific forms without departing from the spirit or essential properties thereof. The present embodiments or examples described above are therefore to be considered in all respects as illustrative and should not be construed limitedly. The scope of the present invention is indicated by the claims and is not bound to any text of the specification. Further, all changes and alterations which belong to the range of equivalent of the claims are intended to be emcompassed within the present invention.

What is claimed is:

1. An oligophosphazene compound, comprising at least one sulfur-containing ring containing a phosphorus atom of a phosphazene skeleton as a constituent atom, wherein
   the sulfur-containing ring is comprised of a residue of a difunctional alkylthiol compound having a thiol group and a group selected from the group consisting of an amino group, a hydroxyl group and a mercapto group.

2. An oligophosphazene compound comprising one or more constituent units U1 represented by the following general formula (I):

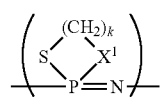

(I)

wherein k is an integer of 1 to 4,

X$^1$ is one selected from the group consisting of an oxygen atom, a sulfur atom, an NH group and an NCH$_3$ group, and each unit U1 is the same or different.

3. The oligophosphazene compound according to claim 2, wherein the number of the same or different constituent units U1 included is an integer of 3 to 14.

4. The oligophosphazene compound according to claim 3, which is a cyclic oligophosphazene compound in which the constituent units U1 are circularly linked.

5. The oligophosphazene compound according to claim 2, further comprising one or more constituent unist U2 represented by the following general formula (II):

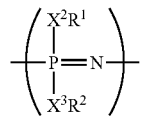

(II)
wherein
each of $X^2$ and $X^3$ is one selected from the group consisting of an oxygen atom, a sulfur atom, an NH group and an $NCH_3$ group,
$R^1$ and $R^2$ each represents a group represented by the following general formula (III):

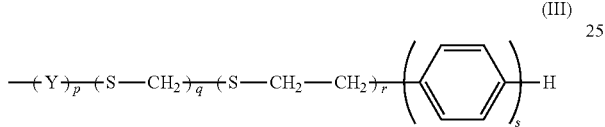

wherein
Y represents one group among the group of a methylene group and an ethylene group,
p is 0 or 1,
each of q and r is an integer of 0 to 5,
s is 0 or 1, n is a positive integer,
the order of each constituent unit is optional, and each unit U2 is the same or different.

6. The oligophosphazene compound according to claim 5, wherein both the number of the constituent units U1 included and the number of the constituent units U2 included are integers and the total number of the constituent units U1 included and the constituent units U2 included as an integer of 3 to 14.

7. The oligophosphazene compound according to claim 6, which is a cyclic oligophosphazene compound in which the constituent units U1 and the constituent units U2 are circularly linked.

8. The oligophosphazene compound according to claim 7, wherein k of the general formula (I) is 2 or 3, the total number of the constituent units U1 included and the constituent units U2 included is an integer of 3 to 4, all of $X^1$, $X^2$ and $X^3$ are NH groups, and in the general formula (III), p is 1, q is 0 or 1 and both r and s are 0.

9. A method for producing an oligophosphazene compound, comprising the step A of applying at least one of the following steps (a-1) and (a-2):
step (a-1): the step of nucleophilically substituting halogen atoms of the phosphonitrile dihalide unit using at least one kind of compound among the group of difunctional alkylthiol compounds having a thiol group and a group selected from the group consisting of an amino group, a hydroxyl group and a mercapto group in the presence of a base capable of scavenging a hydrogen halide; and
step (a-2): the step of nucleophilically substituting halogen atoms of the phosphonitrile dihalide unit using a metal salt of at least one kind of compound among the group of difunctional alkylthiol compounds having a thiol group and one group among the group of a hydroxyl group and a mercapto group,
to a phosphazene compound including a phosphonitrile dihalide unit represented by the following general formula (IV):

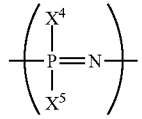

in the general formula (IV), $X^4$ and $X^5$ each represents a halogen atom.

10. The method for producing an oligophosphazene compound according to claim 9, further comprising the step B of applying at least one step of the following steps (b-1) and step (b-2):
step (b-1): the step of nucleophilically substituting halogen atoms of the phosphonitrile dihalide unit using at least one kind of compound selected from the group consisting of a monofunctional alkyl compound having a group selected from the group consisting of an amino group, a hydroxyl group and a mercapto group, a monofunctional thioalkyl compound having a group selected from the group consisting of an amino group, a hydroxyl group and a mercapto group, a monofunctional phenyl compound having a group selected from the group consisting of an amino group, a hydroxyl group and a mercapto group and ammonia in the presence of a base capable of scavenging a hydrogen halide; and
step (b-2): the step of nucleophilically substituting halogen atoms of the phosphonitrile dihalide unit using at least one kind of compound selected from the group consisting of a metal salt of a monofunctional alkyl compound having one group among a hydroxyl group and a mercapto group, a metal salt of a monofunctional thioalkyl compound having one group among a hydroxyl group and a mercapto group and a metal salt of a monofunctional phenyl compound having one group among a hydroxyl group and a mercapto group,
to the phosphazene compound including the phosphonitrile dihalide unit.

11. The method for producing an oligophosphazene compound according to claim 10, wherein the phosphazene compound including the phosphonitrile dihalide unit is a cyclic phosphazene compound in which the phosphonitrile dihalide unit is circularly linked.

12. The method for producing an oligophosphazene compound according to claim 11, wherein the step B is carried out after the step A.

13. The method for producing an oligophosphazene compound according to claim 11, wherein the step A is carried out after the step B.

14. A polymer obtained by thermally polymerizing an oligophosphazene compound, wherein
the oligophosphazene compound comprises at least one sulfur-containing ring containing a phosphorus atom of a phosphazene skeleton as a constituent atom, and the sulfur-containing ring comprised of a residue of a difunctional alkylthiol compound having a group selected from the group consisting of an amino group, a hydroxyl group and a mercapto group.

15. A polymer obtained by thermally polymerizing an oligophosphazene compound according to claim 2.

* * * * *